United States Patent
Frasier et al.

(10) Patent No.: US 10,335,241 B2
(45) Date of Patent: Jul. 2, 2019

(54) METHOD AND APPARATUS FOR INTRAOPERATIVE MEASUREMENTS OF ANATOMICAL ORIENTATION

(71) Applicant: DePuy Synthes Products, Inc., Raynham, MA (US)

(72) Inventors: William Frasier, New Bedford, MA (US); John Riley Hawkins, Cumberland, RI (US); Roman Lomeli, Plymouth, MA (US); Mark Hall, Bridgewater, MA (US); Dennis Chien, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 105 days.

(21) Appl. No.: 14/983,818

(22) Filed: Dec. 30, 2015

(65) Prior Publication Data
US 2017/0189121 A1    Jul. 6, 2017

(51) Int. Cl.
*A61B 34/20* (2016.01)
*G01C 19/00* (2013.01)
(Continued)

(52) U.S. Cl.
CPC .............. *A61B 34/20* (2016.02); *G01C 19/00* (2013.01); *A61B 5/067* (2013.01);
(Continued)

(58) Field of Classification Search
CPC ........ A61B 34/20; A61B 17/56; G01C 19/00; A61F 2/461; A61F 2/4657; A61F 2/38
(Continued)

(56) References Cited

U.S. PATENT DOCUMENTS

| | | |
|---|---|---|
| 5,156,162 A | 10/1992 | Gerhardt |
| 5,251,127 A | 10/1993 | Raab |

(Continued)

FOREIGN PATENT DOCUMENTS

| | | |
|---|---|---|
| EP | 1 943 954 A2 | 7/2008 |
| EP | 2 597 783 A2 | 5/2013 |

(Continued)

OTHER PUBLICATIONS

Delorme, et al., Intraoperative comparison of two instrumentation techniques for the correction of adolescent idiopathic scoliosis. Rod rotation and translation. Spine (Phila PA 1976). Oct. 1, 1999;24(19):2011-7.

(Continued)

*Primary Examiner* — Mouloucoulaye Inoussa
(74) *Attorney, Agent, or Firm* — Nutter McClennen & Fish LLP

(57) ABSTRACT

Electronic devices that detect their position and/or orientation with respect to earth's frame of reference are described. A coupler can removeably maintain the electronic devices in physical proximity of one another. Each electronic device can have a housing and the coupler can be included on the housing and arranged to physically connect the housing of the electronic device to the housing of at least one other electronic device. Alternatively, the coupler can be a packaging that maintains the electronic devices in physical proximity of one another. Each electronic device can be calibrated using the orientation or position information obtained by other electronic devices maintained by the coupler. Further, each electronic device can include a power source that remains inactive until the device is ready for use.

30 Claims, 8 Drawing Sheets

(51) Int. Cl.
  *A61B 5/06* (2006.01)
  *A61B 17/00* (2006.01)
(52) U.S. Cl.
  CPC ............... *A61B 2017/00725* (2013.01); *A61B 2034/2048* (2016.02); *A61B 2034/2051* (2016.02); *A61B 2562/0219* (2013.01); *A61B 2562/0223* (2013.01)
(58) Field of Classification Search
  USPC .......................... 606/88; 623/22.15; 702/150
  See application file for complete search history.

(56) References Cited

U.S. PATENT DOCUMENTS

| | | | |
|---|---|---|---|
| 5,291,901 | A | 3/1994 | Graf |
| 5,305,203 | A | 4/1994 | Raab |
| 5,329,933 | A | 7/1994 | Graf |
| 5,748,767 | A | 5/1998 | Raab |
| 6,015,409 | A | 1/2000 | Jackson |
| 6,514,219 | B1 | 2/2003 | Guimond et al. |
| 6,585,519 | B1 | 5/2003 | Benesh |
| 6,711,432 | B1 | 3/2004 | Krause et al. |
| 6,715,213 | B2 | 4/2004 | Richter |
| 7,001,346 | B2 | 2/2006 | White |
| 7,139,601 | B2 | 11/2006 | Bucholz et al. |
| 7,559,931 | B2 | 7/2009 | Stone |
| 7,611,522 | B2 | 11/2009 | Gorek |
| 7,634,119 | B2 | 12/2009 | Tsougarakis et al. |
| 7,634,306 | B2 | 12/2009 | Sarin et al. |
| 7,706,000 | B2 | 4/2010 | Cohen et al. |
| 7,918,887 | B2 | 4/2011 | Roche |
| 7,956,887 | B2 | 6/2011 | Hoeg et al. |
| 7,957,809 | B2 | 6/2011 | Bourget et al. |
| 7,974,677 | B2 | 7/2011 | Mire et al. |
| 7,981,115 | B2 | 7/2011 | Justis et al. |
| 8,057,479 | B2 | 11/2011 | Stone |
| 8,057,482 | B2 | 11/2011 | Stone et al. |
| 8,128,662 | B2 | 3/2012 | Altarac et al. |
| 8,167,823 | B2 | 5/2012 | Nycz et al. |
| 8,442,621 | B2 | 5/2013 | Gorek et al. |
| 8,549,888 | B2 | 10/2013 | Isaacs |
| 8,565,853 | B2 | 10/2013 | Frigg et al. |
| 8,690,888 | B2 | 4/2014 | Stein et al. |
| 8,888,821 | B2 | 11/2014 | Rezach et al. |
| 9,198,698 | B1 | 12/2015 | Doose et al. |
| 9,554,411 | B1 | 1/2017 | Hall et al. |
| 9,579,043 | B2 | 2/2017 | Chien et al. |
| 9,993,177 | B2 | 6/2018 | Chien et al. |
| 2002/0035321 | A1 | 3/2002 | Bucholz et al. |
| 2004/0152970 | A1 | 8/2004 | Hunter et al. |
| 2005/0166410 | A1 | 8/2005 | Richter et al. |
| 2005/0222793 | A1 | 10/2005 | Lloyd et al. |
| 2005/0251026 | A1 | 11/2005 | Stone |
| 2005/0262911 | A1 | 12/2005 | Dankowicz et al. |
| 2006/0100508 | A1 | 5/2006 | Morrison |
| 2006/0247773 | A1 | 11/2006 | Stamp |
| 2008/0103557 | A1 | 5/2008 | Davis et al. |
| 2008/0177203 | A1 | 7/2008 | von Jako |
| 2008/0228195 | A1 | 9/2008 | von Jako et al. |
| 2008/0269767 | A1 | 10/2008 | O'Brien |
| 2008/0292161 | A1 | 11/2008 | Funk et al. |
| 2009/0171328 | A1 | 7/2009 | Horvath |
| 2009/0249851 | A1 | 10/2009 | Isaacs |
| 2010/0010494 | A1 | 1/2010 | Quimo |
| 2010/0036384 | A1 | 2/2010 | Gorek et al. |
| 2010/0069919 | A1 | 3/2010 | Carls et al. |
| 2010/0087823 | A1 | 4/2010 | Kondrashov |
| 2010/0100011 | A1 | 4/2010 | Roche |
| 2010/0191088 | A1 | 7/2010 | Anderson et al. |
| 2010/0204575 | A1 | 8/2010 | Roche et al. |
| 2010/0204955 | A1 | 8/2010 | Roche et al. |
| 2010/0312103 | A1 | 12/2010 | Gorek et al. |
| 2011/0040340 | A1 | 2/2011 | Miller et al. |
| 2011/0125196 | A1 | 5/2011 | Quevedo et al. |
| 2011/0196455 | A1* | 8/2011 | Sieracki ............ A61N 1/36071 607/62 |
| 2011/0270262 | A1 | 11/2011 | Justis et al. |
| 2011/0275957 | A1 | 11/2011 | Bhandari |
| 2011/0295159 | A1 | 12/2011 | Shachar et al. |
| 2012/0035868 | A1 | 2/2012 | Roche et al. |
| 2012/0065497 | A1 | 3/2012 | Brown et al. |
| 2012/0095330 | A1 | 4/2012 | Shechter et al. |
| 2012/0112690 | A1 | 5/2012 | Stulen et al. |
| 2012/0123252 | A1 | 5/2012 | Brunner |
| 2012/0203140 | A1 | 8/2012 | Malchau et al. |
| 2012/0232834 | A1 | 9/2012 | Roche et al. |
| 2013/0079679 | A1 | 3/2013 | Roche et al. |
| 2013/0079680 | A1 | 3/2013 | Stein et al. |
| 2013/0165940 | A1* | 6/2013 | DiSilvestro ............ A61F 2/461 606/88 |
| 2013/0241468 | A1 | 9/2013 | Moshfeghi |
| 2013/0268007 | A1 | 10/2013 | Rezach et al. |
| 2014/0031829 | A1 | 1/2014 | Paradis et al. |
| 2014/0052149 | A1 | 2/2014 | van der Walt et al. |
| 2014/0057572 | A1 | 2/2014 | Klinghult et al. |
| 2014/0088607 | A1 | 3/2014 | Recknor |
| 2014/0171965 | A1 | 6/2014 | Loh et al. |
| 2014/0232333 | A1 | 8/2014 | Kim et al. |
| 2014/0275981 | A1 | 9/2014 | Selover et al. |
| 2014/0276871 | A1 | 9/2014 | Sherman et al. |
| 2014/0303522 | A1 | 10/2014 | Akimoto et al. |
| 2015/0057733 | A1 | 2/2015 | Lotfi |
| 2015/0137746 | A1 | 5/2015 | Lee et al. |
| 2015/0150646 | A1 | 6/2015 | Pryor et al. |
| 2015/0305786 | A1 | 10/2015 | Wehrle et al. |
| 2015/0313566 | A1 | 11/2015 | Diers et al. |
| 2016/0007909 | A1* | 1/2016 | Singh .................... A61F 2/4657 606/102 |
| 2016/0058320 | A1 | 3/2016 | Chien et al. |
| 2016/0058523 | A1 | 3/2016 | Chien et al. |
| 2016/0235480 | A1 | 8/2016 | Scholl et al. |
| 2016/0262800 | A1 | 9/2016 | Scholl et al. |
| 2017/0143426 | A1 | 5/2017 | Isaacs et al. |
| 2017/0194820 | A1 | 7/2017 | Hall et al. |
| 2017/0231709 | A1 | 8/2017 | Gupta et al. |
| 2018/0070860 | A1 | 3/2018 | Gupta et al. |
| 2018/0256067 | A1 | 9/2018 | Chien et al. |

FOREIGN PATENT DOCUMENTS

| | | |
|---|---|---|
| EP | 2 901 957 A1 | 8/2015 |
| GB | 190927693 A | 9/1910 |
| JP | 2000-254141 A | 9/2000 |
| WO | 99/15097 A2 | 4/1999 |
| WO | 2005/077000 A2 | 8/2005 |
| WO | 2013/053398 A1 | 4/2013 |
| WO | 2013/169674 A1 | 11/2013 |
| WO | 2014/025305 A1 | 2/2014 |
| WO | 2014/063181 A1 | 5/2014 |
| WO | 2015/003224 A1 | 1/2015 |
| WO | 2015/114119 A1 | 8/2015 |
| WO | 2016/032875 A1 | 3/2016 |

OTHER PUBLICATIONS

Ghanem, et al., Intraoperative optoelectronic analysis of three-dimensional vertebral displacement after Cotrel-Dubousset rod rotation. A preliminary report. Spine (Phila PA 1976). Aug. 15, 1997;22(16):1913-21.

International Search Report and Written Opinion for Application No. PCT/US2015/046217, dated Nov. 9, 2015 (11 pages).

Lafon, et al., Intraoperative three-dimensional correction during rod rotation technique. Spine (Phila PA 1976). Mar. 1, 2009;34(5):512-9. doi: 10.1097/BRS.0b013e31819413ec.

Lafon, et al., Intraoperative three dimensional correction during in situ contouring surgery by using a numerical model. Spine (Phila PA 1976). Feb. 15, 2010;35(4):453-9. doi: 10.1097/BRS.0b013e3181b8eaca. Abstract.

Luc Duong, et al., Real time noninvasive assessment of external trunk geometry during surgical correction of adolescent idiopathic scoliosis. Scoliosis. Feb. 24, 2009;4:5. doi: 10.1186/1748-7161-4-5.

(56) References Cited

OTHER PUBLICATIONS

Mac-Thiong, et al., A new technique for intraoperative analysis of trunk geometry in adolescent idiopathic scoliosis. Can J Surg. Jun. 2002;45(3):219-23.
Mac-Thiong, et al., The effect of intraoperative traction during posterior spinal instrumentation and fusion for adolescent idiopathic scoliosis. Spine (Phila PA 1976). Jul. 15, 2004;29(14)1549-54.
International Search Report and Written Opinion for Application No. PCT/US2016/067134, dated Sep. 11, 2017 (20 pages).
Written Opinion for Application No. PCT/US2017/050023, dated Jan. 8, 2018 (J&J No. MED5026WOPCT) (4 Pages).
Invitation to Pay Additional Fees for Application No. PCT/US2016/067134, dated Jun. 26, 2017 (14 pages).
International Search Report and Written Opinion for Application No. PCT/US2016/067140, dated Mar. 23, 2017 (13 pages).
International Search Report and Written Opinion for Application No. PCT/US2017/017344, dated Jul. 13, 2017 (22 pages).
U.S. Appl. No. 14/471,120, filed Aug. 28, 2014, Systems and Methods for Intraoperatively Measuring Anatomical Orientation.
U.S. Appl. No. 14/934,237, filed Nov. 6, 2015, Systems and Methods for Intraoperatively Measuring Anatomical Orientation.
U.S. Appl. No. 15/263,023, filed Sep. 12, 2016, Systems and Methods for Anatomical Alignment.
U.S. Appl. No. 15/375,307, filed Dec. 12, 2016, Systems and Methods for Wirelessly Powering or Communicating with Sterile-Packed Devices.
U.S. Appl. No. 15/429,566, filed Feb. 10, 2017, Systems and Methods for Intraoperatively Measuring Anatomical Orientation.

\* cited by examiner

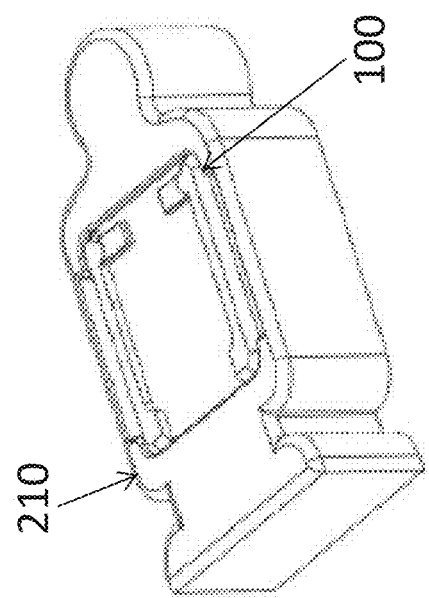
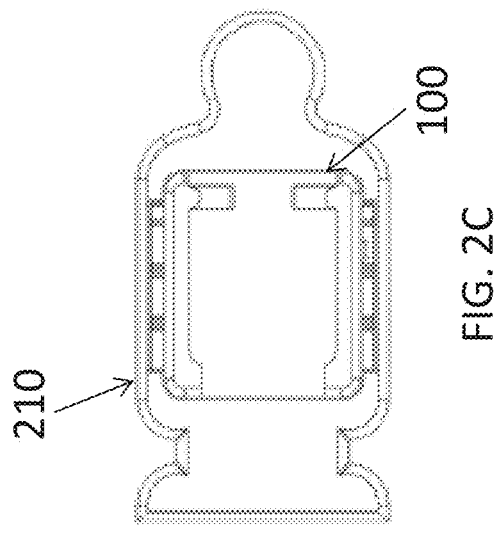
FIG. 2B
FIG. 2C

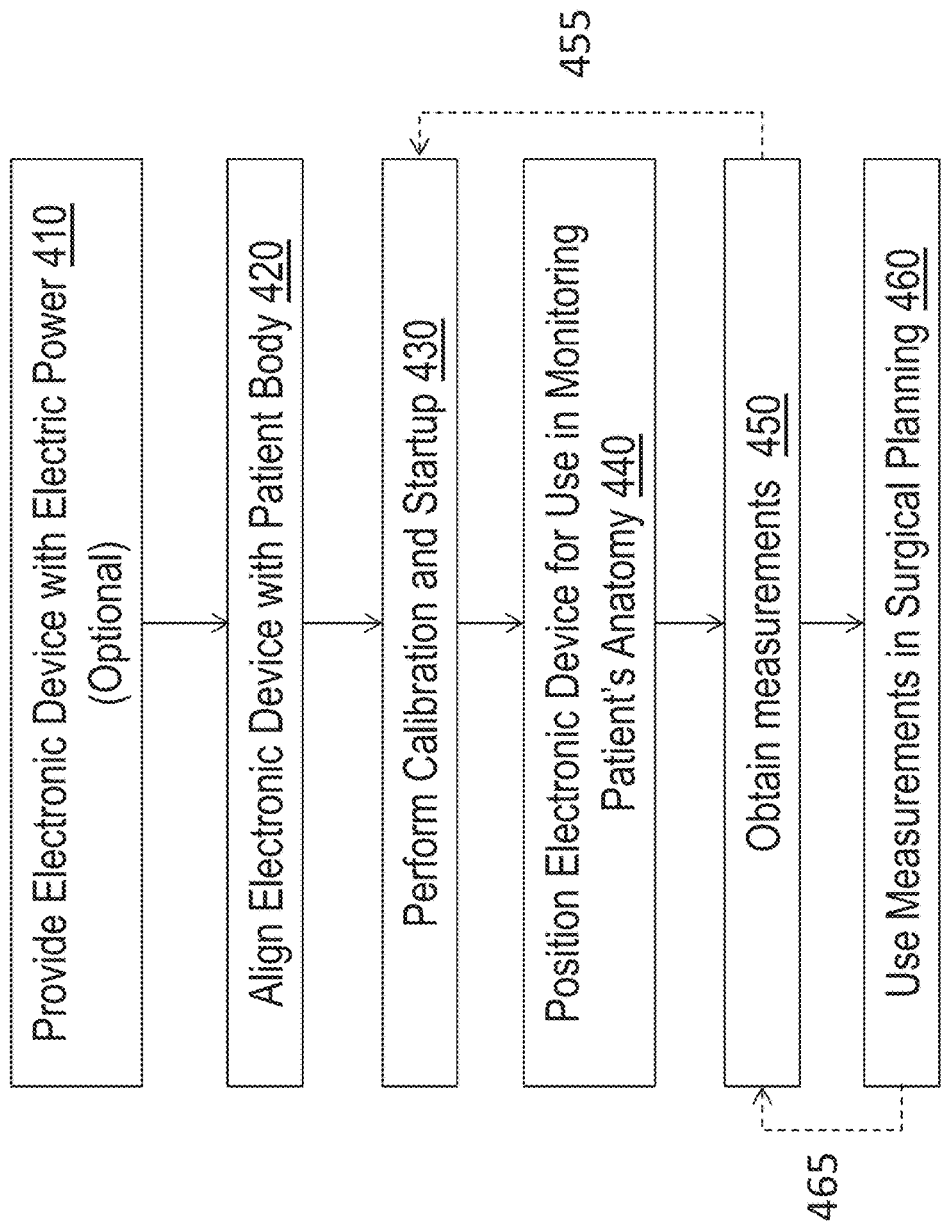

METHOD AND APPARATUS FOR INTRAOPERATIVE MEASUREMENTS OF ANATOMICAL ORIENTATION

FIELD

The present disclosure generally relates to measuring orientation and/or position of a patient's anatomy during surgery.

BACKGROUND

Medical practitioners (e.g., surgeons) often need to assess the position and/or orientation of a patient's anatomy while performing medical procedures (e.g., surgery). For example, a surgeon may require information regarding the position and/or orientation of a patient's bones with respect to the patient or a reference coordinate system in order to visualize the patient's anatomy and/or determine the position/orientation in which medical instruments used to assist in performing the medical procedure should be positioned. Further, medical practitioners performing medical procedures in which the patient's anatomy is being altered (e.g., a traditional pedicle subtraction osteotomy, which can involve removal of a portion of the bone in the vertebra of the patient) may need to assess the amount of change that is being made to the patient's anatomy at any given point of time during the medical procedure.

Although imaging techniques (e.g., CT-scans, x-rays, etc.) can be used to plan for a desired anatomical correction to the patient's body (pre-operation) and/or determine whether the desired anatomical correction has been achieved (post-operation), intraoperative imaging to determine the on-going changes to the patient's anatomy can be difficult, inconvenient, and result in interruption of the medical procedure. For example, when performing an operation to correct an anatomical issue in a patient's spine, intraoperative assessment of the changes in the patient's anatomy, using traditional imaging techniques, may require the medical practitioner to pause the medical procedure (e.g., step back from the operating table and allow an imaging device to be brought in) so that an image of the patient's anatomy can be obtained.

Further, most traditional imaging techniques tend to only provide snapshots of the patient's anatomical structure. Although these snapshots can illustrate progressive changes to the patient's anatomy in a quantitative manner, they do not provide data of the changes as they occur in real-time. Additionally, depending on how the imaging device is positioned, the obtained image can be a subjective representation of the patient's anatomy. Therefore, when used intraoperatively, the surgeon performing the surgery may need to make a subjective assessment of when a desired anatomical orientation has been achieved. This can result in sub-optimal patient outcomes and repeat surgeries due to over- or under-correction with respect to the planned correction.

Exemplary systems and methods for intraoperatively measuring anatomical orientation using electronic devices are disclosed in U.S. application Ser. No. 14/471,120 filed on Aug. 28, 2014, which is hereby incorporated by reference in its entirety. There is a continual need for improved ways of packaging, calibrating, and testing surgical electronic devices, improving the accuracy of such devices, and for making such devices more user-friendly.

SUMMARY

Systems and method for measuring the position or orientation of a surgical instrument or patient anatomy using electronic devices are disclosed herein, as are various ways of packaging, calibrating, and testing such devices.

Systems and methods according to the embodiments described herein relate to determining at least one of an orientation or a position of a device with respect to earth's frame of reference. In one aspect, an apparatus comprising a plurality of electronic devices and a coupler is described. Each electronic device can detect at least one of an orientation or a position of the electronic device with respect to earth's frame of reference. The coupler is configured to removeably maintain the plurality of electronic devices in physical proximity of one another. The coupler maintains the plurality of electronic devices in at least one of a similar orientation or a similar position.

In another aspect, a system comprising a plurality of electronic devices, a coupler, and a processor configured to communicate with the plurality of electronic devices is described. Each electronic device can detect at least one of an orientation or a position of the electronic device with respect to earth's frame of reference. The coupler is configured to removeably maintain the plurality of electronic devices in physical proximity of one another. The coupler maintains the plurality of electronic devices in at least one of a similar orientation or a similar position. The processor can communicate with the plurality of electronic devices and can control calibration of each electronic device using orientations or positions detected by other electronic devices.

In yet another aspect, a method for determining at least one of an orientation or position of a medical instrument or an orientation or position of an anatomical feature on a patient that includes coupling an electronic device to the medical instrument or the feature of the patient's anatomy is described. The electronic device can be a device selected from among a plurality of electronic devices each configured to detect at least one of an orientation or a position of the electronic device with respect to earth's frame of reference. The plurality of electronic devices can be removeably coupled to one another in at least one of a similar orientation or a similar position and in physical proximity of one another. The described method also includes determining at least one of the orientation or position of the medical instrument or the orientation or position of the feature of the patient's anatomy based on the orientation or the position detected by the electronic device coupled thereto.

In other examples, any of the aspects above, or any system, method, apparatus, and computer program product method described herein, can include one or more of the following features.

The coupler can maintain each electronic device in an orientation in which the electronic device is expected to detect the orientation or position most accurately. Each electronic device can include a housing. The coupler can be included on the housing and can physically connect the housing of the electronic device to housing of at least one other electronic device. The housing can include one or more features for connecting the electronic device to at least one of a location within an operating room, a medical instrument in the operating room, a location on body of a patient, or for aligning the apparatus with an anatomical feature of the patient in the operating room. The coupler can connect the housing of the electronic device to the housing of the at least one other electronic device using at least one of a mechanical connection or a magnetic connection. The housing can include one or more markings configured to assist a user in aligning the electronic device with the body of the patient.

The coupler can allow movement of at least one electronic device to a desired projection plane and the processor can use a quaternion generated based on the movement of the electronic device to define a projection plane used for controlling calibration of the electronic device. Alternatively or additionally, the coupler can be to maintain the plurality of electronic devices in a predetermined similar orientation and the processor can use a fixed quaternion value representing the orientation of the electronic devices to define a projection plane used for controlling calibration of each electronic device.

The coupler can include a packaging that maintains the plurality of electronic devices in at least one of physical proximity of one another or a specific physical orientation with respect to one another. The packaging can be at least one of round or human body-shaped. The packaging can include one or more markings configured to assist a user in aligning the plurality of electronic device with the body of the patient. The packaging can include one or more features for maintaining each electronic device within the packaging. The packaging can include a temperature controller configured to maintain the electronic device at a predetermined temperature. Each electronic device can include an internal power source. The internal power source can be configured to remain inactive while the electronic device is maintained by the packaging. The internal power source can be configured to be activated once the electronic device is removed from the packaging.

Each electronic device can include an internal power source. The internal power source can be configured to remain inactive while the electronic device is maintained by the coupler. The internal power source can be configured to be activated once the electronic device is detached from the coupler. The internal power source can be connected to at least one of a removable pull-tab or a magnetic reed switch and configured such that the internal power source remains inactive prior to at least one of removal of the pull-tab or activation of the magnetic reed switch and becomes activated upon removal of the pull-tab or activation of the magnetic reed switch.

Each electronic device can include a cover configured to removeably cover at least a portion of the electronic device. The cover can be connected to a switch. The switch can activate the internal power source upon removal of the cover. The internal power source can be arranged such that it remains inactive prior to removal of the cover.

Each electronic device can include a temperature controller that maintains the electronic device at a predetermined temperature. The electronic device can further include a communications interface that reports the detected orientation or position of the electronic device to a computing device that makes use of the detected orientation or position information.

Each electronic device can include an interface that is arranged to transfer at least one of power from an external power source to the electronic device or data between the electronic device and an external processor.

Other aspects and advantages of the invention can become apparent from the following drawings and description, all of which illustrate the principles of the invention, by way of example only.

BRIEF DESCRIPTION OF THE DRAWINGS

The invention will be more fully understood from the following detailed description taken in conjunction with the accompanying drawings, in which:

FIG. 2B is a perspective view of the example packaging shown in FIG. 2A.

FIG. 2C is a top view of the example packaging shown in FIG. 2B.

FIG. 4 is an example flow diagram of procedures for using an electronic device in a medical procedure according to the embodiments disclosed herein.

DETAILED DESCRIPTION

Systems and method for measuring the position or orientation of a surgical instrument or patient anatomy using electronic devices are disclosed herein, as are various ways of packaging, calibrating, and testing such devices.

Figure 1A:
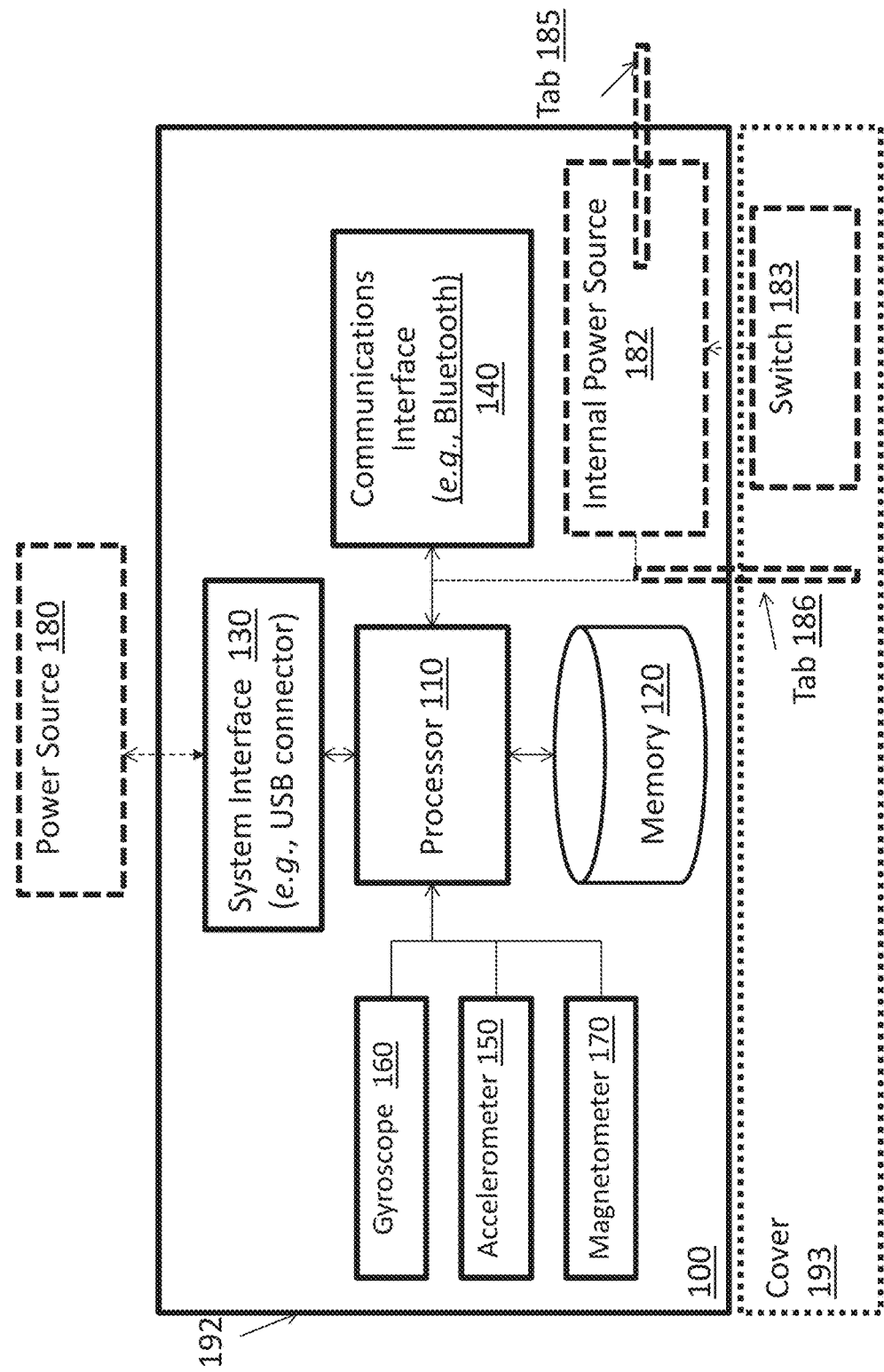
FIG. 1A is a block diagram of an example electronic device that can be used with the embodiments disclosed herein.
Figure 1B:
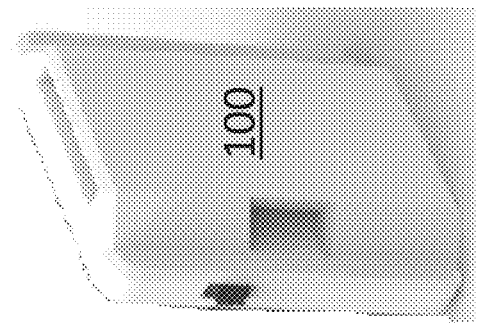
FIG. 1B illustrates an example electronic device that can be used with the embodiments disclosed herein.
Figure 1C:
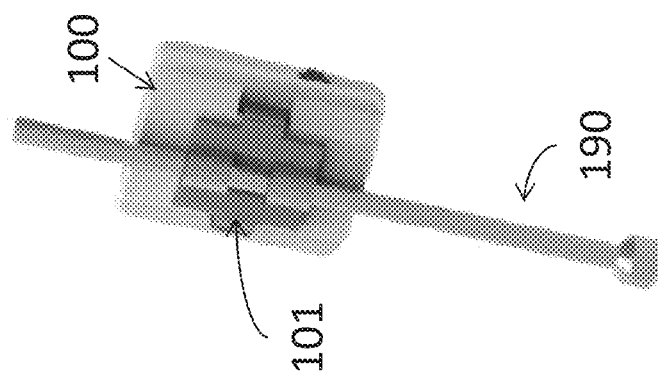
FIG. 1C illustrates the example electronic device of FIG. 1B as attached to a surgical instrument.
Figure 1D:
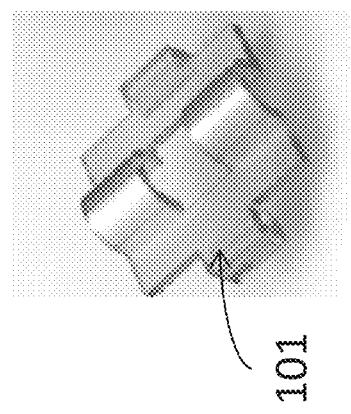
FIG. 1D illustrates a connector that can be used connect the electronic device of FIG. 1B to the surgical instrument shown in FIG. 1C.

FIG. 1A is a block diagram of an example electronic device 100 that can be used with the embodiments disclosed herein. FIGS. 1B-1C and 1E-1G demonstrate other examples of the electronic device 100. FIG. 1D illustrates an example connector that can be used to couple an electronic device 100 to a surgical instrument.

Referring to FIG. 1A, the electronic device 100 can include components such as a processor 110, a memory 120, a system interface 130, and a communications interface 140. The electronic device 100 can also include various components configured for obtaining and/or detecting information regarding the orientation and position of the electronic device 100. For example, the electronic device 100 can include an accelerometer 150 (e.g., a 9-axis accelerometer for measuring one or more angles of the electronic device 100 with respect to a reference point such as the earth), a gyroscope 160 or a gyroscopic sensor, and a magnetometer 170. The electronic device 100 can be implemented in digital electronic circuitry or computer hardware.

The components included in the electronic device 100 can be arranged such that they communicate with one another to detect, obtain, process, communicate, and/or store information regarding the position and/or orientation of the electronic device 100 and one or more surgical devices 190 (shown in FIG. 1C) to which the electronic device 100 can be attached. The components shown in FIG. 1A, and any other component that can be used with the electronic device 100, can be included within housing 192 of the electronic device 100 and/or be positioned external to the housing 192 of the electronic device 100.

The processor 110 can be any processor known in the art and include a microcontroller, a microcomputer, a programmable logic controller (PLC), a field-programmable gate array (FPGA), an application specific integrated circuit (ASIC), integrated circuits generally referred to in the art as a computer, and/or other programmable circuits.

The processor 110 can be coupled to the memory 120, which can include a random access memory (RAM), a read-only memory (ROM), a flash memory, a non-transitory computer readable storage medium, and so forth. The memory 120 can store instructions for execution by the processor 110 to implement the systems disclosed herein or to execute the methods disclosed herein. Additionally or alternatively, the memory 120 can store information regarding the position and/or orientation of the electronic device 100, calculated by the processor 110 or obtained by other components of the electronic device 100, and/or received from an external device through the communications interface 140. The memory 120 can also store calibration information for the components included in the electronic device 100.

The processor 110 can be in communication with a system interface 130 and a communications interface 140 (e.g., Bluetooth). The system interface 130 can, for example, be a Universal Serial Bus (USB) connector. The system interface 130 can be connected to an external power source 180 such as an electric charger (e.g., power adapter) and/or a power terminal. The USB connector 130 can be arranged such that it can connect to one or more peripherals (e.g., USB cable) that connect the electronic device 100 to the power supply 180. Alternatively or additionally, the electronic device 100 can include an internal power supply 182 (e.g., battery, for example a lithium ion battery) that provides the electronic device 100 with electronic power.

The communications interface 140 can be configured to receive and transmit information to/from any of the processor 110, the memory 120, or other internal or external components and devices (e.g., another surgical electronic module, a base station, etc). The communications interface 140 can be wireless (e.g., near-field communication (NFC), Wi-Fi, Bluetooth, Bluetooth LE, ZigBee, etc.) or wired (e.g., USB or Ethernet). In the case of NFC, for example, electronic device 100 can include a radio transceiver (not shown) configured to communicate with a radio transceiver of another device (e.g., a second module, using one or more standards, such as ISO/IEC 14443, FeliCa, ISO/IEC 18092, and those defined by the NFC Forum). The communication interface 140 can be selected to provide the desired communication range. Bluetooth (e.g., class 2 Bluetooth having a range of 5-10 meters) can be used for the communication interface to allow the electronic device 100 to remain somewhat distant from the device with which it is communicating (e.g., the second module and/or a base station, while at the same time limiting the communication range such that other mobile devices unlikely to be used in the surgery are not needlessly involved).

As noted, the processor 110 can be communicatively coupled with the accelerometer 150, gyroscope 160, and magnetometer 170 and arranged such that it can obtain information regarding the position and/or orientation of the electronic device 100 from these components and/or perform various calculations based on the positional/orientation information detected by these components. Specifically, the gyroscope 160 can be used to measure the current orientation of the electronic device 100 in three dimensions in an inertial frame of reference. The accelerometer 150 can also be used along with the gyroscope to measure acceleration, inclination, and movements of the electronic device in three dimensions. The magnetometer 170 (or a magnetic sensor) can further be used to determine the positioning of the electronic device 100 relative to the magnetic north (i.e., the magnetic heading of the electronic device 100). The processor 110 can combine and process the information obtained from the accelerometer 150, gyroscope 160, and the magnetometer 170 to determine the absolute position and/or orientation of the electronic device 100 in three dimensions. The processor 110 can also calculate a relative position and/or orientation of the electronic device 100 with respect to an external reference point based on the absolute position and/or orientation of the electronic device 100.

The processor 110 can be configured to detect an absolute position and/or orientation of the module in the spherical coordinate system with the earth as reference. Additionally or alternatively, the processor 110 can be configured to detect the positional information at intervals throughout a surgical procedure, for example every second, every millisecond, every microsecond, etc., such that the positional/orientation information is effectively detected continuously and in real-time. The positional/orientation information can be detected regularly, intermittently, or at non-regular intervals. The positional/orientation information can be conveyed to the user (e.g., surgeon), stored in the memory 120, conveyed to the processor 110 for processing, and/or communicated to one or more external devices via the communications interface 140 for processing or storage. In some embodiments, the electronic device 100 can include an electronic display mounted in or on a housing of the electronic device. Alternatively, or in addition, the electronic display can be disposed remotely from the electronic device, for example in a user device as discussed further below.

The processor 110 can be configured to determine both an orientation and a position (e.g., a distance of the electronic device 100 from some reference point) by being configured to switch between an orientation detection mode in which the processor 110 only detects the orientation and a full detection mode in which the processor 110 detects both the orientation and the position. The electronic device 100 can be configured to switch between the orientation detection mode and the full detection mode at the request of the user, for example via actuation of an input device (not shown) connected to the electronic device 100, and/or based on an identity of the surgical device to which the electronic device 100 is attached.

The positional information detected and/or calculated by the electronic device 100 can include one or more angles of the electronic device 100 with respect to the earth (absolute angle), one or more angles of the module with respect to a some other reference point (relative angle), distances between the electronic device 100 and one or more external reference points, changes in any of these values, a rate of changes in any of these values, and/or higher order derivatives of any of these values. The electronic device 100 can be configured to detect and/or calculate the positional information in a variety of units and coordinate systems. To provide relevant anatomical measurements during surgery, the electronic device 100 can be configured to translate positions and/or orientations detected in a conventional spherical coordinate system into positions and/or orientations along conventional sagittal, axial, and coronal planes.

Figure 1E:
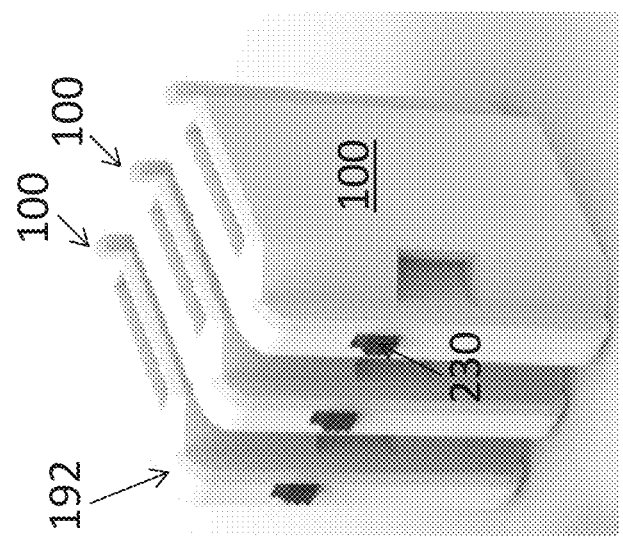
FIG. 1E illustrates an example embodiment in which multiple electronic devices, of the type shown in FIG. 1B, are coupled with one another.
Figure 1G:
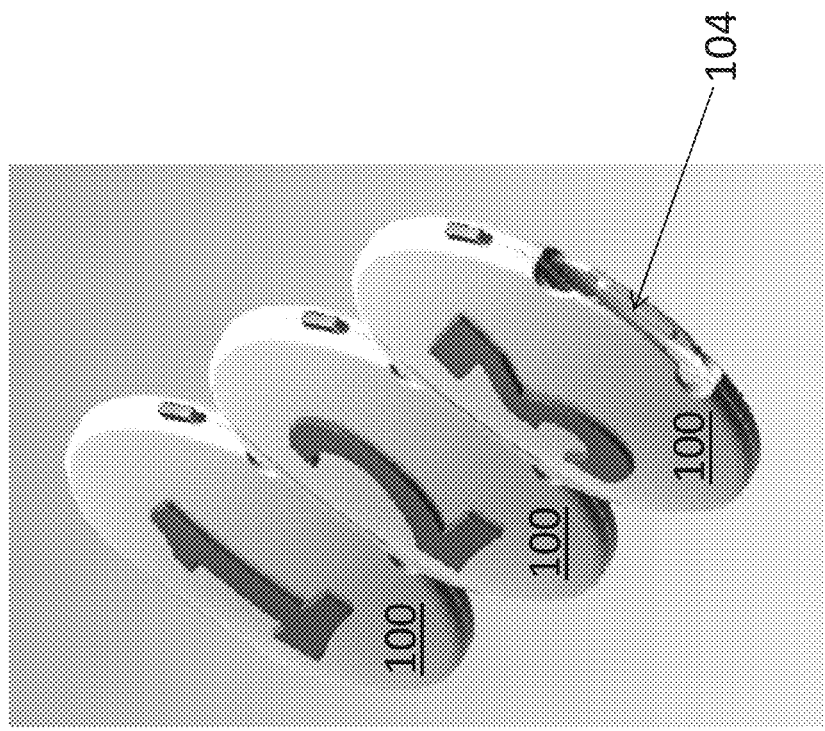
FIG. 1G illustrates an example embodiment in which multiple electronic devices, of the type shown in FIG. 1F, are coupled with one another.
Figure 1F:
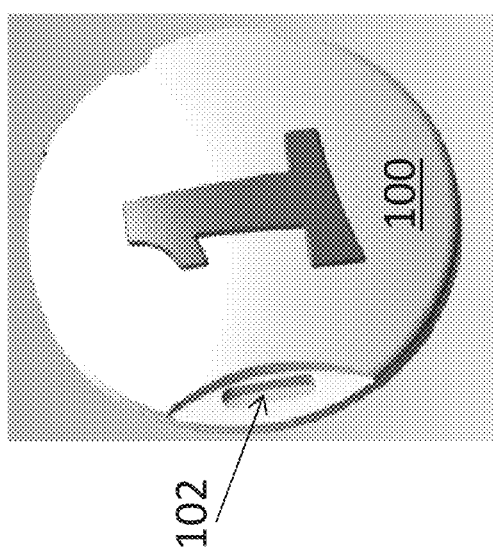
FIG. 1F illustrates an example electronic device in which the electronic device includes a housing having a generally round shape.

The electronic device 100 can further include a housing 192. The housing 192 can assume any size and shape. For example, as shown in FIG. 1B, FIG. 1C, and FIG. 1E, the housing 192 be generally box-shaped (e.g., rectangular or square). Additionally or alternatively, the electronic device 100 can assume any other shape and/or be amorphous. For example, FIG. 1F and FIG. 1G illustrate examples in which the housing 192 of the electronic device assumes a generally round shape.

The housing 192 of the electronic device 100 can be arranged to facilitate the coupling of two or more electronic devices 100 to one another. For example, as shown in FIGS. 1F and 1G, the electronic device 100 can include one or more slots 104 and/or corresponding tabs 102 that are configured to facilitate coupling of the electronic devices 100 to one another. The tab 102 can be a snap tab and configured such that it allows the electronic devices 100 to snap into one another. FIG. 1G illustrates an example in which three electronic devices 100 (labeled as 1, 2, and 3) have been coupled with one another.

Further, as illustrated in FIG. 1C, the housing 192 can be configured such that it facilitates the coupling of the electronic device 100 with one or more surgical devices 190. It will be appreciated that the electronic device 100 can be formed integrally with a surgical device, or can be selectively coupled or attached thereto. Exemplary surgical devices include surgical instruments (e.g., drivers, rongeurs, forceps, distractors, retractors, and the like) and surgical implants (e.g., bone anchors, bone plates, fixation or stabilization rods and other hardware, joint replacement implants, intervertebral cages, and the like). The electronic device 100 can also be configured to attach directly to an anatomy of a patient. The electronic device 100 can be attached to screws used in performing spinal surgery (e.g., pedicle screws) and/or to a driver shaft that attaches to the pedicle screws. Further, when performing surgical operations that alter the shape or size of a bone (e.g., osteotomy), one or more sensors can be positioned on each side of the area to which the alteration is being applied (e.g., each side of the osteotomy). Alternatively or additionally, additional sensors can be positioned on various portions of the patient's body (e.g., at one or both ends of a patient's spinal column) to measure the global position or orientation to which the alteration is being applied. Additional electronic devices 100 can be utilized. For example, additional electronic devices 100 can be attached to various parts of the patient's body, the surgical bed, or at any position remote from the surgical site. Additional electronic devices 100 can also be mounted on any of the surgical tools used in performing the surgery.

The electronic device 100 can be attached to the surgical device 190 using any technique known in the art, for example, using a connector 101, similar to that illustrated in FIG. 1D. The housing 192 can include one or more features that can both facilitate the coupling of the electronic device 100 with one or more surgical instruments 190 and allow for coupling of two or more electronic devices 100 with one another. FIG. 1E illustrates another example in which multiple electronic devices 100 are connected to one another. The housings of the electronic devices can include complementary shapes such that they nest with each other. Alternatively or in addition to the features included on the housing 192, two or more electronic devices 100 can be coupled to one another using any type of attachment known in the art, for example mechanical and/or magnetic attachments.

Further, as described in U.S. application Ser. No. 14/471,120 filed on Aug. 28, 2014, the entire teachings of which are incorporated herein by reference, the electronic device 100 can continually detect changes in a position and/or orientation of the surgical device 190 during surgery and communicate the detected changes to a user (e.g., medical practitioners performing the surgery). The surgical device 110 can be attached to a portion of a patient's anatomy and/or be used to manipulate the patient's anatomy. The electronic device 100 can detect the changes in the position and/or orientation of the surgical device 190 by quantitatively measuring changes in the position and/or orientation of the surgical instrument 190, or of an anatomical structure to which the electronic device 100 or the surgical instrument 190 are connected, during surgery.

In embodiments that incorporate more than one electronic device 100, the electronic devices 100 can continually detect changes in their positions and/or orientations relative to one another. These detected changes can be interpreted by the electronic devices 100 to determine the changes in relative positions and/or orientations of the surgical device(s) 190 to which the electronic devices 100 are attached. Additionally or alternatively, at least one of the electronic devices 100 can help to establish a reference 3D location in the operating room, particularly where the at least one electronic device is stationary.

As noted, the electronic device 100 and its components can be implemented in hardware, for example on chip. Depending on the type of hardware used to implement the electronic device 100, the accuracy of the positional information obtained from the electronic device 100 may depend on the position/orientation at which the electronic device 100 and its components are positioned. Accordingly, embodiments disclosed herein orient the electronic device 100 and its components within its housing 192 such that the orientation expected to yield optimal (e.g., more accurate) positioning information is aligned with the plane of interest for the patient. Some orientation-sensing hardware, for example, is more accurate in one plane or dimension that in others. Accordingly, such hardware or the printed circuit board to which it is mounted can be oriented within the housing 192 such that, when the housing is aligned with the patient according to the system instructions or external markings on the housing, the more-accurate measurement dimension of the hardware is aligned with the dimension of primary interest for the surgical procedure being performed.

The housing 192 can assume various shape and forms. For example, the housing 192 can be box-shaped, rounded, amorphous, or be in the shape of the human body or body part. Alternatively or additionally, the housing 192 can be in the form of a sticker or tape that can be affixed to or coupled with a person's (patient's) body. Generally, the housing 192 can assume any shape or form that facilitates the usage of the electronic device 100 in the application or the procedure in which the electronic device 100 is being used. For example, an electronic device 100 that assumes the form of a sticker or adhesive tape can be adhered or otherwise attached to the patient. Once attached or placed on the patient body, the electronic device 100 can be used to determine the position and orientation of the location to which the electronic device 100 is adhered and/or serve as a reference point. For example, the electronic device 100 can be affixed to a relatively stationary portion of the patient's body (e.g., close to a relatively stationary part of the patient's bony anatomy) and serve as a reference point to connect the positional measurements to other measurements, for example those obtained using x-ray or other imaging techniques. The housing (e.g., sticker) 192 can have properties that allow the electronic device 100 to be visible when using imaging techniques to obtain three dimensional (3D) images of the surgical site. For example, the electronic devices 100 can be visible in X-ray Fluoroscopy, thereby allowing the location and orientation of the electronic devices 100 to be visible in the 3D images obtained using this technique. The sticker can be in the form of a map that corresponds with the packaging in which a plurality of electronic devices 100 are disposed. In this manner, the sticker can serve as a diagrammatic guide to assist the user in placing each electronic device included in the packaging in the correct position for a given procedure.

Figure 2A:
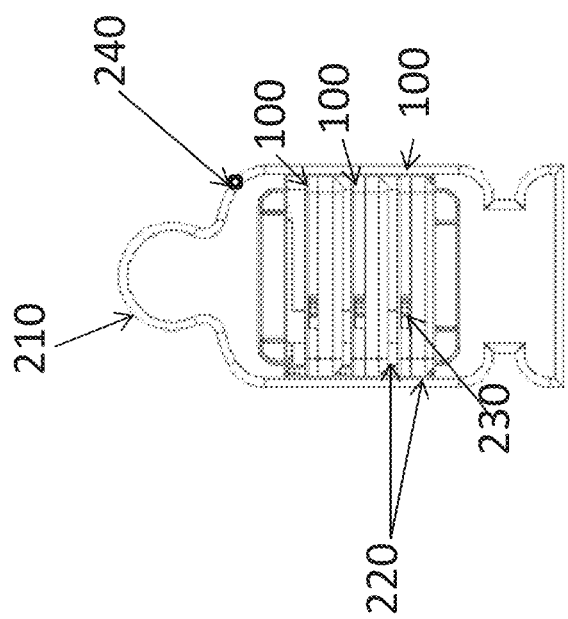
FIG. 2A is an example of a packaging that can be used with the electronic device shown in FIG. 1B.

The electronic device 100 can be packaged in a packaging that is separate from the housing 192 of the electronic device 100. FIG. 2A is an example of a human body-shaped packaging 210 that can be used with the embodiments disclosed herein. In the embodiment shown in FIG. 2A, multiple electronic devices 100 are packaged into a single packaging 210. The packaging 210 can assume any shape (e.g., generally box-shaped, amorphous, etc.) or size. For example, as shown in FIG. 2, the packaging 210 can be human-shaped. The human-shaped packaging 210 can facilitate the usage of the electronic device 100 since the surgeon or medical practitioner can simply align the packaging 210 with the patient's body. For example, the packaging 210 can be arranged that such an axis (e.g., the caudal axis) of the packaging is brought into alignment with a corresponding axis (e.g., the caudal axis) of the patient once a portion of the packaging (e.g., the head of the human-shaped packaging) is aligned with a corresponding portion of the patient's body (e.g., the head of the patient). Such arrangement can assist with registering the axes of the electronic device 100 with corresponding axes in the patient's body, thereby facilitating the alignment of the electronic device 100 with the patient's body. The controlling software in 330 can be programmed with the packaging configuration such that the relative alignment of all the sensors is known. For example, the operating table can be assumed to be parallel to the ground, the package can have a flat bottom, and the sensors can know their position with respect to gravity such that once the package axis is aligned with the cranial/caudal axis of the patient, the system can match the coordinate systems of the sensors to the coordinate system of the patient and allow for a single step calibration method. The operating table can be manipulated such that the head can be higher or lower than the feet, but not axially rotated, such that a rotational axis reference can be established with the flat bottom package resting on the patient at the beginning of the procedure.

Each packaging 210 can contain one or more electronic devices 100. For example, in the embodiment shown in FIG. 2A, the human-shaped packaging 210 is shown as including three electronic devices 100. Each electronic device 100 included in the packaging can utilize data obtained from the other electronic devices 100 in the package to calibrate itself. Calibration of the electronic devices 100 can be done in various ways. For example, the calibration of the electronic device can generally involve using acceleration and magnetic data obtained from the accelerometer 150 and magnetometer 170 to determine information regarding the orientation of the electronic device 100 and using the changes in the orientation information to calibrate the gyroscope 160.

Further, the embodiments disclosed herein can orient each electronic device 100 within the packaging 210 in a position and/or orientation expected to yield optimal (e.g., more accurate) positioning information. The electronic devices 100 can be packaged in an orientation that provides the highest accuracy in calibration-related use. Specifically, as noted, depending on the type of hardware used to implement the electronic device 100, each electronic device 100 can be more accurate in one direction than in other directions. Therefore, embodiments disclosed herein achieve more accurate calibration results by orienting the electronic devices 100 within the packaging 210 such that the axes of the electronic devices 100 that are expected to yield the more accurate results are aligned with the plane of interest for the patient.

The packaging 210 can have one or more markings (not shown) that can be used to create alignment with patient. The markings can allow alignment to a patient in the sagittal or transverse plane. Additionally or alternatively, the packaging 210 can include one or more notches 220 (e.g., jigs) that maintain and/or force the electronic devices 100 into alignment with one another and also with the packaging 210. The alignment notches 220 can also simultaneously maintain the electronic devices 100 in alignment during calibration.

Although shown in FIG. 2A as including more than one electronic device, the packaging 210 can include a single electronic device. FIG. 2B illustrates a perspective view of an example human-shaped packaging 210 that contains a single electronic device 100. FIG. 2C illustrates a top view of the human-shaped packaging shown in FIG. 2B that includes a single electronic device. As shown in FIG. 2A, the packaging 210 can include one or more notches 220 (e.g., jigs) that maintain and/or force the electronic device 100 into alignment with the packaging 210.

The packaging 210 can be positioned on any location on the patient's body or placed/mounted at any location within the area in which the medical procedure is being performed. For example, the packaging 210 can be temporarily mounted to the patient's bed or patient's bedrail to assist in alignment of the patient with the packaging 210, and the electronic device(s) 100 disposed therein, and also to ensure that the packaging 210 and its electronic device(s) 100 are not shifted during the medical procedure.

The packaging 210 can include various features for positioning/attaching the packaging 210 to the patient's body or a location within the surgical site. For example, the packaging can include an adhesive feature that can be used to attach the packaging to a desired location (e.g., adhesive sticker, double-sided tape, etc.) or a clamp that can be used to attach the packaging to a location within the surgical site (e.g., patient's bed or bedrail).

The packaging 210 can include one or more features for indicating successful calibration of the electronic device(s) 100. Alternatively or additionally, the features 230 for indicating successful calibration can be included on the housing of the electronic device 100 and/or be a component included in the electronic device 100. The indicator means 230 can include light, tone/sound, and/or vibration features that light up, generate a tone, and/or vibrate upon successful calibration of each electronic device 100 and/or once all of the devices included in packaging 210 have been successfully calibrated.

The packaging 210 can be arranged such that it allows for verification of successful calibration of the electronic device(s) 100 and for determining whether any errors in the calibration process have occurred. For example, the packaging 210 can be in the form of a circular block that can hold one or more electronic devices 100 and can rotate the electronic devices 100 about a common axis. This allows for verification of accuracy of the gyroscope 160 included in each of the electronic devices 100. Specifically, since the electronic devices 100 included in the packaging 210 share a common axis, if a gyroscope 160 included in an electronic device 100 included in a package 210 provides a reading that is different from the other electronic devices 100 in that package 201, that electronic device can be marked/labeled as one that requires calibration and/or as an unstable electronic device. Similarly, the measurements obtained from the accelerometer 150 of each electronic device 100 can be compared against the reading obtained from the rest of the electronic devices 100 and an electronic device 100 whose accelerometer 150 detects an angular acceleration that is different from the angular acceleration obtained by the other electronic devices can be marked as unstable and/or in need of calibration. The marking/labeling of the electronic device as one that requires calibration and/or as an unstable electronic device can be done using an application program that runs on a computer within the operating room (described later with respect to FIG. 3). Alternatively, or in addition, the system can apply a software correction to the discrepant electronic device.

Although the calibration and verification procedures disclosed above are described with respect to one or more electronic devices that are held in a common packaging 210, these procedures can be carried out without requiring the sensors to be contained in the packaging 210. Specifically, as shown in FIG. 1E and described above, the electronic devices 100 can be coupled to one another using mechanical or magnetic attachments. The coupled electronic devices 100 can be arranged such that they allow for verification of successful calibration of each electronic device(s) 100 and for determining whether any errors in the calibration process have occurred. Further, the electronic devices can be coupled such that they share a common axis so that each electronic device 100 can use information obtained from the other electronic devices to calibrate. Specifically, since the coupled electronic devices 100 share a common axis, if a gyroscope 160 included in an electronic device 100 provides a reading that is different from the other electronic devices 100 to which that device is coupled, that electronic device can be marked/labeled as one that requires calibration and/or as an unstable electronic device. Similarly, the measurements obtained from the accelerometer 150 of each electronic device 100 can be compared against the reading obtained from the rest of the electronic devices 100 and an electronic device 100 whose accelerometer 150 detects an angular acceleration that is different from the angular acceleration obtained by the other electronic devices can be marked as unstable and/or in need of calibration.

Once calibrated, the electronic devices 100 can be removed from the packaging 210 and/or uncoupled from one another (e.g., coupled configurations shown in FIGS. 1E and 1G) and used within the operating site. Once removed, if an electronic device 100 requires further calibration, it can simply be attached back to other electronic devices 100 and/or placed back within the housing 210.

The physical connection between the electronic devices 100 in a device pack (e.g., coupled configurations shown in FIGS. 1E and 1G) and/or the proximity achieved by maintaining the electronic devices 100 within a single housing can allow the electronic devices 100 to communicate with one another so that they can calibrate (or re-calibrate). Specifically, the electronic devices 100 can include at least one of a magnetic, physical, or electronic (e.g., Bluetooth, Near Field Communication (NFC)) switch that triggers the resetting of the electronic device 100 once the electronic device 100 is connected to other electronic devices and/or placed in the packaging 210. The resetting or "zeroing" of the electronic device 100 allows a user to selectively set an initial relative position and/or orientation of the electronic device 100 to zero. Subsequent changes in the relative positions and/or orientations of the electronic device 100 can be measured and displayed to the user so that the user knows when a desired change in position and/or orientation of the modules has been reached.

Referring back to FIG. 1A, the internal power source 182 included in the electronic device 100 can be a deferred action power source, such as a deferred action battery. Deferred action batteries allow activation of the electronic device at the time of use, thereby preventing the battery of the device from draining itself prior to being used. The deferred action power source can employ any of a variety of deferred action features. For example, the deferred action power source can be a power source having a removable barrier that is configured to isolate various portions of a battery cell (e.g., the electrodes and the electrolyte) from one another. The barrier can be arranged such that as long as the barrier is in place, the battery 182 remains inactive. However, once removed, the portions of the battery 182 that were previously isolated come in contact with one another, thereby activating the battery 182. The barrier can be a fragile barrier that can be broken or removed to activate the battery 182. For example, the barrier can be formed, at least in part, of plastic, paper, or similar fragile materials.

The barrier can include a portion 185 that extends out of the electronic device 100 so that the barrier can be manipulated and/or removed as a function of manipulation of the portion that extends out of the electronic device 100. For example, the barrier can include a pull-tab 185 that extends out of the electronic device 100 and arranged such that the removal and/or manipulation of the pull-tab 185 (e.g., tearing, pulling, shaking, etc.) results in manipulation of the barrier and activation of the battery 182. The pull-tab can be attached to the packaging of the electronic device 100 such that the pull-tab is automatically actuated to connect the power supply when the electronic device is removed from the packaging.

Alternatively or additionally, the electronic device 100 can have an internal power source 182 that is remotely activated. For example, the electronic device 100 can include a battery 182 that can be activated by shaking the electronic device 182.

In some implementations, the electronic device 100 can include an internal power source 182 that remains inactive as long as the electronic device 100 remains in the packaging 210 and/or as long as the electronic device 100 remains attached to other electronic devices. The internal power source 182 can be arranged such that it is activated upon removal of the electronic device 100 from the packaging 210 and/or upon uncoupling the electronic device 100 from being attached to other electronic devices.

As noted, the electronic device can include means for coupling (e.g., tabs 102 and slots 104 shown in FIGS. 1F-1G) the electronic device to other electronic devices (e.g., magnetic connections, mechanical connections) and/or be maintained in a packaging using holding means, such as jigs 220. The internal power source 182 can be arranged such that the power source 182 remains inactive as long as the coupling means (e.g., 102, 104) remain engaged to connect the electronic device 100 to other electronic devices 100 and/or as long as the holding means (e.g., jigs) 220 are being used to maintain the electronic device within the packaging.

In some implementations, alternatively or in addition to a deferred action power source, the electronic device can include one or more features for separating or disconnecting the power source 182 from the electronic device to ensure that the power source 182 is only active, in use, or connected while the electronic device is in use. For example, the electronic device 100 can include a feature, such as a pull-tab 186, that separates the power source 182 (e.g., battery) from the electronic device 100 (or the circuit included in the electronic device). The feature can be arranged such that removal and/or manipulation of the pull-tab 186 (e.g., tearing, pulling, shaking, etc.) can result in creating and/or establishing a connection between the power source 182 and the circuit of the electronic device 100, thereby providing electronic power to the electronic device 100.

In some implementations, the electronic device can include a power source that remains disconnected from the electronic circuit of the electronic device as long as the electronic device remains in the packaging 210 and/or as long as the electronic device remains attached to other electronic devices. The power source 182 can be arranged such that it establishes a connection with the electronic circuit of the electronic device 100 to provide electronic power to the electronic device upon removal of the electronic device 100 from the packaging 210 and/or upon uncoupling the electronic device from being attached to other electronic devices.

As noted, the electronic device can include features for coupling (e.g., tabs 102 and slots 104 shown in FIGS. 1F-1G) the electronic device to other electronic devices (magnetic connections, mechanical connections) and/or be maintained in a packaging using holding means 220, such as jigs. The internal power source 182 can be arranged such that the power source 182 remains disconnected from the electronic device (i.e., disconnected from the electronic circuit including the components included in the electronic device 100) for as long as the coupling means 102, 104 remain engaged to connect the electronic device to other electronic devices and/or as long as the holding means 220 (e.g., jigs) are being used to maintain the electronic device within the packaging 210. The power source 182 can be arranged such that once removed from the packaging and/or disengaged, the power source 182 can establish a connection to the electronic circuit of the electronic device to provide the electronic device with electronic power.

In some implementations, the power source 182 can be controlled by a switch 183 that can be used to activate or deactivate the power source 182 so that the power source 182 remains inactive and unconsumed as long as the switch 183 remains inactive. Alternatively or additionally, the switch 183 can be used to connect or disconnect the power source 182 from the electronic device. The switch 183 can be a reed switch, such as a magnetic reed switch. The magnetic reed switch 183 can be arranged such that it remains inactive while the device 100 is attached to other electronic devices 100 and/or as long as the device 100 remains in the packaging 215 and becomes activated once the device 100 is removed from the packaging 215 and/or is uncoupled from other electronic devices 100. The magnetic reed switch 183 can be a magnetically actuated reed switch 183 and include a magnet (not shown) that is arranged to transition the reed switch between closed and open positions. For example, the magnetic reed switch can include a magnet that maintains the switch in the open position as long as the electronic device 100 is attached to other electronic devices 100 and/or as long as the device 100 remains in the packaging 215. The magnet can be further arranged such that the removal of the electronic device 100 from the packaging 215 and/or uncoupling of the electronic device 100 from other electronic devices 100 can cause the magnet to close the switch 183 and connect the power source 182 of the electronic device 100 to the other components of its electronic circuit. The switch 183 can be any type of switch known in the art. The magnet can further be any type magnet, including magnets in which a magnetic field can be induced. The switch 183 and/or magnet can be remotely controllable such that the switch and/or magnet can be remotely activated (e.g., closing of the switch) or deactivated. For example, the switch 183 or the magnet can be controllable using a wireless Bluetooth connection.

In some embodiments, the electronic device can include reed switch disposed between an internal power source of the electronic device and the electronic device's logic board or other circuitry. The electronic device can be sterilized and/or stored prior to use in a box or other packaging that includes a magnet aligned with the reed switch to maintain the reed switch in an open position. Upon removal of the electronic device from the packaging, the magnet disposed in the packaging is moved out of proximity with the reed switch, causing the reed switch to transition to a closed position and thereby supply power from the internal power source to the logic circuitry of the electronic device. Accordingly, the battery can be "remotely" coupled to the other circuitry of the electronic device, avoiding the need for a switch that requires a housing penetration. This can be desirable to help with sterilization of the device and maintain the sterility of the device.

In some embodiments, the electronic device 100 can include a cover 193. The cover 193 can be a part of the housing or separate from the housing. The cover 193 can be arranged such that it covers at least a portion of the housing. The electronic device 100 can be arranged such it is activated upon the removal of the cover 193. For example, the cover 193 can be arranged such that its removal triggers the activation of the switch 183 and/or the power source 182, as described above. The cover 193 may be mechanically or magnetically coupled to a switch 183 and or power source 182. In some embodiments, the electronic device 100 can include a spring-loaded plunger that is held down by the cover and/packaging. The packaging and/or the cover 183 can be arranged such that removal of the electronic device from the packaging and/or opening/removal of the cover causes the plunger to spring out and activate the internal power source 182.

The electronic device 100 can be configured to automatically begin a calibration routine when power is first supplied thereto.

Figure 3:
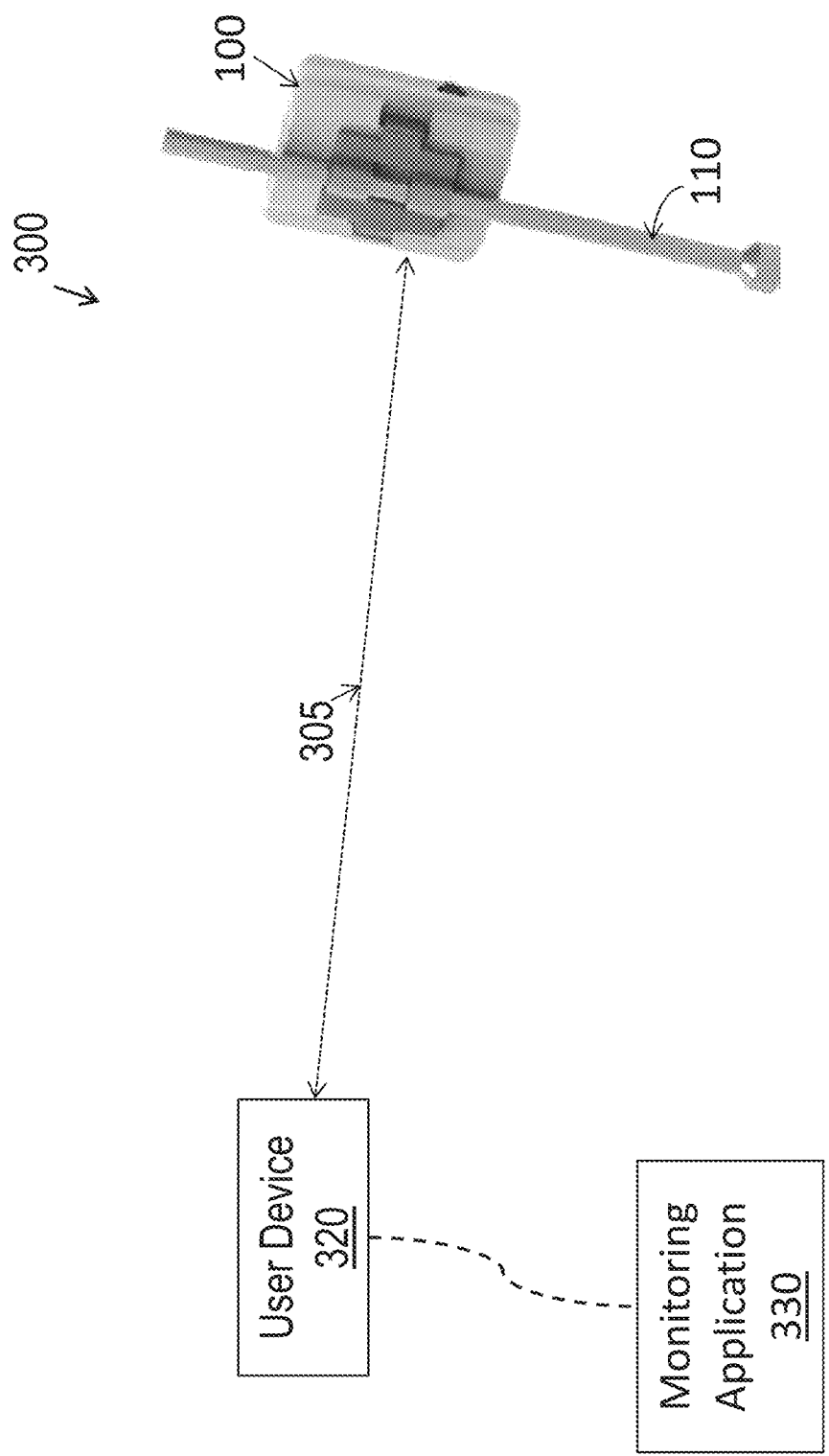
FIG. 3 is block diagram of an intraoperative measurement system that can be used with the embodiments disclosed herein.

FIG. 3 is a block diagram of an intraoperative measurement system 300 that can be used with the embodiments disclosed herein. The intraoperative measurement system 300 can include one or more user devices 320 that connect with the electronic device 100 or one or more electronic devices 100 to control, manage, and use the device 100 to obtain information regarding the patient's anatomical orientation and/or position.

As shown in FIG. 3, a user (not shown, such as a medical practitioner or a surgeon) can use the user device 320 to connect with the electronic device 100. The user device 320 can be any type of a communications device that is capable of establishing direct or indirect communication link 305 with other devices (e.g., electronic device 100). For example, the user device 320 can include Bluetooth capabilities that enable the user device 320 to communicate with other Bluetooth compatible devices (e.g., electronic device 100). Alternatively or additionally, the communications device 320 can connect with other devices through a communication network (not shown, e.g., the Internet, a private network (e.g., local area network (LAN)). The communications device 320 can connect to other devices wirelessly or through a wired link.

Examples of the user devices 320 that can be used with the embodiments described herein include, but are not limited to, wireless phones, smart phones, desktop computers, workstations, tablet computers, laptop computers, handheld computers, personal digital assistants, etc. Each user device 320 can have a screen that may be used to receive and display information. The screen can be a touch screen. Each user device 320 can further include a monitoring application 330 that can be used for controlling the electronic device 100 and/or receiving (e.g., orientation and/position information) or transmitting (e.g., calibration information, initialization or resetting information) to/from the electronic device 100. The monitoring application 330 can be used to analyze the information received from the electronic device 100 and/or present the user with information that could be used for intraoperative surgical planning (e.g., estimated post-operative outcome). For example, the monitoring application 330 can employ a predictive model to provide an estimate of the amount of correction that can be achieved from a given surgical adjustment.

The information retrieval application 330 can be presented to the user of the user device 320 using a user interface (not shown). Additionally or alternatively, the information retrieval application 230 can be presented to the user using application software that provides an interactive medium for receiving input from the user. The information retrieval application 330 can be a web-based platform. Alternatively or additionally, the user device 320 can access the information retrieval application 330 through an interactive medium provided by the application software or using the web-based interface.

FIG. 4 is an example flow diagram of procedures for using an electronic device 100 in a medical procedure according to the embodiments disclosed herein. The procedures shown in FIG. 4 need not occur in any specific order and can occur in any order.

As noted the electronic device 100 can be powered using an external power source 180 (e.g., a USB connection-based power source) and/or an internal power source 182. Further, as noted, the electronic device 100 can remain inactive and only activated once it is ready for use. For example, the electronic device can be provided with power 410 by activating a switch 183 and/or manipulating a tab 185, 186 to connect the electronic components included in the electronic device 100 with an electronic power source 180, 182.

Further, as noted above, the electronic device 100 can be included in a housing 192 or a packaging 210 that facilitates the alignment of the electronic device 100 with the patient's body. Specifically, since depending on the type of hardware used to implement the electronic device 100, the accuracy of the positional information obtained from the electronic device 100 may depend on the position/orientation at which the electronic device 100 and its components are positioned, embodiments disclosed herein orient the electronic device 100 and its components within its housing 192 such that the orientation expected to yield optimal positioning information is aligned with the plane of interest for the patient. The housing 192 or packaging 210 can be marked or shaped in a manner intended to assist with aligning the electronic device 100 with the patient's body. For example, the housing 192 and/or packaging 210 can be box-shaped, rounded, amorphous, or be in the shape of the human body and/or in the form of a sticker or tape that can be affixed to or coupled with a person's (patient's) body. The surgeon can use the shape or the markers to align the packaging 210 or housing 192 with the patient's body. The packaging 210 and/or the housing 192 can also have markings that can be used to define alignment to the patient in sagittal or transverse plane and/or force the electronic devices 100 into alignment.

The electronic device 100 (or devices, if multiple devices are used) can be calibrated 430. The electronic device 100 can utilize data obtained from the other electronic devices 100 in the package to calibrate itself. Alternatively or additionally, the electronic device 100 can receive the required calibration data from the user through the user device 320. During the calibration procedure for defining the projection plane, the electronic devices can be placed aligned to each other and the electronic devices can be calibrated to each other. Further, one electronic device can be rotated about the normal to a desired projection plane and a quaternion generated can be entered into the calibration algorithm to define the projection plane. If the electronic devices are aligned to each other and aligned in a known orientation to the desired projection plane for the first step, the physical rotation can be skipped and a fixed quaternion value can be placed into the calibration algorithm representing the rotation, removing the need for the physical step to be performed.

As noted, the electronic devices 100 can stay attached to each other through mechanical or magnetic attachment, thereby forcing a certain sequence of use and calibration and fixing their orientation for calibration. The electronic devices can be attached to each other via their packaging 210 and/or by being physically attached through connections, such as mechanical or magnetic connections.

Further, separating each electronic device 100 from other devices in the cluster (electronic devices in a packaging or a group of connected electronic devices) can trigger that electronic device to turn on. The sequence in which the electronic devices are removed from the cluster can automatically inform the monitoring application 330 as to the use of each electronic device (e.g., electronic device #1 is being attached to a certain tool, electronic devices #2 is being attached to a sacrum, etc.). If the user determines that a device 100 needs to re-calibrated, at any time during use, the electronic device 100 can simply be connected back into the cluster 455 to prompt a recalibration workflow in the monitoring application 330. Reconnecting the electronic devices causes the electronic devices to be placed back in a same plane of reference to assist with calibration relative to each other. The electronic devices can be configured such that once connected they can recalibrate, using a magnetic, physical, or electronic (e.g., Bluetooth/NFC near field communication) switch that triggers a reset in the electronic devices and causes them to recalibrate with respect to each other once they are physically connected to each other. Further, the electronic devices can be configured such that all connected electronic devices in a cluster reset every time a new one is added to the cluster to ensure that all are calibrated to each other properly.

The electronic devices can further be checked for errors before they are used in the medical procedure. For example, an error check can be performed on the electronic devices contained in a cluster by rotating the electronic devices in the cluster around the same axis and checking the accuracy of the electronic devices against each other. For example, a circular block that holds all the electronic devices and rotates them about a common axis can be used to check the accuracy of each of the gyroscopes included in each electronic device against other gyroscopes. If one electronic device appears to produce different results, that device can be recalibrated, marked as unusable, or have a software correction applied thereto. The accelerometers or other components of the electronic devices can also be verified during the error check to ensure that they all produce similar measurements when rotated to similar angular accelerations.

A warm up time sequence can also be applied to the electronic device based on the operating room temperature and/or the preferred operating temperature. The warm up sequence can be initialized, monitored, or controlled by the monitoring application 330 of the user device 320. The startup sequence can be arranged such that it delays the sensing functions of the electronic device 100 and/or returns an error code until a predetermined warm up time has passed. The predetermined time can be any amount of time that may be required for the electronic device 100 to achieve its suitable operating temperature. This predetermined amount of time can be set by the user and/or through the use of the monitoring application 330.

The monitoring application 330 can also be arranged to monitor the internal temperature of the electronic device 100, the cluster of the electronic devices 100, the packaging 210, and/or the ambient temperature and make any required arrangements for delaying the use of the electronic device 100 and/or generating an error code until the electronic device 100 has reached its proper operating temperature.

Further, the packaging 210 and/or the electronic devices 100 can have a warmer 240 (shown in FIG. 2A) that is arranged to maintain the electronic devices 100 at a desired/optimal working temperature. The warmer 240 can be a stand-alone unit in the packaging 210 and/or a part of the circuitry included in the electronic device and/or its housing. The warmer 210 can be connected to the monitoring application 330 such that it can be initialized, controlled, and/or monitored by the monitoring application 330. Alternatively, the heat needed to bring the electronic device to its desired operating temperature can be supplied by the components included in the electronic device 100 and/or a heating element or power source (e.g, battery) disposed in the packaging 210 or in the housing 190. Alternatively or additionally, the electronic device 100 can include the required components (e.g., a Peltier device) for cooling the electronic device, its housing 192, or packaging 210 to ensure that the temperature of the electronic device 100 is maintained at a point so that the most optimal (accurate) measurements can be obtained.

The calibration, initialization, error check, and/or startup procedures described herein can be initialized and/or controlled by the monitoring application 330 of the user device 320.

Once initialized, the electronic device(s) 100 can be positioned in the operating room for use in obtaining measurements 440. As noted, the sequence in which the electronic devices are removed from the cluster/packaging can automatically inform the monitoring application 330 as to the use of each electronic device. Alternatively or additionally, the user can use the monitoring application to record, monitor, and/or control the positions at which the electronic devices 100 are disposed.

The electronic devices 100 can be used in obtaining measurements during the operation 450 and these measurements can be used in planning the medical procedure at hand 460. New and updated measurements can be obtained 465 as the electronic devices are moved during the medical procedure.

It will further be appreciated by a person skilled in the art that the devices and methods described herein can be particularly useful for robotic assisted surgery. For example, one or more surgical electronic modules as described herein can transmit positional information to a robotic manipulator, which can manipulate the one or more modules until they have reached a desired final position that has been input to the manipulator.

While the systems and methods disclosed herein are generally described in the context of spinal surgical procedures on a human patient, it will be appreciated that they can be readily used in other types of surgery, on non-human patients, or in fields unrelated to surgery.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

In the present disclosure, like-numbered components of the embodiments generally have similar features and/or purposes. Further, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the size and shape of the components with which the systems and devices are being used, the anatomy of the patient, and the methods and procedures in which the systems and devices will be used. The figures provided herein are not necessarily to scale. It will be understood that the devices and methods specifically described herein and illustrated in the accompanying drawings are non-limiting example embodiments. The features illustrated or described in connection with one example embodiment may be combined with the features of other embodiments. Such modifications and variations are intended to be included within the scope of the present disclosure.

The invention claimed is:

1. An apparatus comprising:
a plurality of electronic devices, each electronic device including an internal power source and being configured to detect at least one of an orientation or a position of the electronic device with respect to earth's frame of reference in a plurality of dimensions; and
a coupler configured to removeably maintain the plurality of electronic devices in physical proximity of one another, the coupler maintaining the plurality of electronic devices in at least one of a similar orientation or a similar position;
wherein the internal power source of the electronic device is configured to be deactivated when at least a portion of the coupler is in proximity to the electronic device.

2. The apparatus of claim 1, wherein the coupler is configured to maintain each electronic device in an orientation in which the electronic device is expected to detect the orientation or position most accurately.

3. The apparatus of claim 1, wherein each electronic device includes a housing, the coupler being included on the housing and configured to physically connect the housing of the electronic device to housing of at least one other electronic device.

4. The apparatus of claim 3, wherein the housing includes one or more features for connecting the electronic device to at least one of a location within an operating room, a medical instrument in the operating room, a location on body of a patient, or for aligning the apparatus with an anatomical feature of the patient in the operating room.

5. The apparatus of claim 3, wherein the coupler is configured to connect the housing of the electronic device to the housing of the at least one other electronic device using at least one of a mechanical connection or a magnetic connection.

6. The apparatus of claim 3, wherein the housing includes one or more markings configured to assist a user in aligning the electronic device with the body of the patient.

7. The apparatus of claim 1, wherein the coupler comprises a packaging, the packaging being configured to maintain the plurality of electronic devices in at least one of physical proximity of one another or a specific physical orientation with respect to one another.

8. The apparatus of claim 7, wherein the packaging is at least one of round or human body-shaped.

9. The apparatus of claim 7, wherein the packaging includes one or more markings configured to assist a user in aligning the plurality of electronic devices with the body of the patient.

10. The apparatus of claim 7, wherein the packaging includes one or more features for maintaining each electronic device within the packaging.

11. The apparatus of claim 7, wherein the packaging includes a temperature controller configured to maintain the electronic device at a predetermined temperature.

12. The apparatus of claim 7, wherein the internal power source is configured to be activated once the electronic device is removed from the packaging.

13. The apparatus of claim 1, wherein the internal power source is configured to be activated once the electronic device is detached from the coupler.

14. The apparatus of claim 1, wherein each electronic device includes at least one of a removable pull-tab or a magnetic reed switch that is any of mechanically and magnetically coupled to at least a portion of the coupler such that the internal power source remains inactive prior to at least one of removal of the pull-tab or activation of the magnetic reed switch and becomes activated upon at least one of removal of the pull-tab or activation of the magnetic reed switch.

15. The apparatus of claim 1, wherein each electronic device includes a cover configured to removeably cover at least a portion of the electronic device, the cover being connected to the coupler and a switch configured to activate the internal power source.

16. The apparatus of claim 1, wherein each electronic device includes a temperature controller configured to maintain the electronic device at a predetermined temperature.

17. The apparatus of claim 1, wherein each electronic device includes a communications interface, the communications interface being configured to report the detected orientation or position of the electronic device to a computing device that makes use of the detected orientation or position information.

18. The apparatus of claim 1, wherein each electronic device includes an interface arranged to transfer at least one of power from an external power source to the electronic device or data between the electronic device and an external processor.

19. A system comprising:
a plurality of electronic devices, each electronic device including an internal power source and being configured to detect at least one of an orientation or a position of the electronic device with respect to earth's frame of reference in a plurality of dimensions;
a coupler configured to removeably maintain the plurality of electronic devices in physical proximity of one another, the coupler maintaining the plurality of electronic devices in at least one of a similar orientation or a similar position; and
a processor configured to communicate with the plurality of electronic devices; and
a non-transitory computer readable storage medium configured to communicate with the processor and containing instructions that, when executed by the processor, cause the processor to control calibration of each electronic device using orientations or positions detected by other electronic devices;
wherein the internal power source of the electronic device is configured to be deactivated when at least a portion of the coupler is in proximity to the electronic device.

20. The system of claim 19, wherein the coupler is arranged to allow movement of at least one electronic device to a desired projection plane and the processor is configured to use a quaternion generated based on the movement of the electronic device to define a projection plane used for controlling calibration of the electronic device.

21. The system of claim 19, wherein the coupler is arranged to maintain the plurality of electronic devices in a predetermined similar orientation and the processor is configured to use a fixed quaternion value representing the orientation of the electronic devices to define a projection plane used for controlling calibration of each electronic device.

22. The system of claim 19, wherein the electronic device includes a housing, the coupler being included on the housing and configured to physically connect the housing of the electronic device to housing of at least one other electronic device.

23. The system of claim 22, wherein the housing includes one or more features for connecting the electronic device to at least one of a location within an operating room, a medical instrument in the operating room, or a location on body of a patient in the operating room.

24. The system of claim 22, wherein the coupler is configured to connect the housing of the electronic device to the housing of the at least one other electronic device using at least one of a mechanical connection or a magnetic connection.

25. The system of claim 19, wherein the coupler comprises a packaging, the packaging being configured to maintain the plurality of electronic devices in at least one of physical proximity of one another or a specific orientation with respect to one another.

26. The system of claim 25, wherein the packaging is at least one of round or human body-shaped.

27. The system of claim 25, wherein the packaging includes a temperature controller configured to maintain the electronic device at a predetermined temperature.

28. The system of claim 25, wherein the internal power source is configured to be activated once the electronic device is removed from the packaging.

29. The system of claim 19, wherein the internal power source is configured to be activated once the electronic device is detached from the coupler.

30. The system of claim 19, wherein the electronic device includes an interface arranged to transfer at least one of power from an external power source to the electronic device or data between the electronic device and an external processor.

\* \* \* \* \*